United States Patent
Wiess

(10) Patent No.: US 7,048,744 B2
(45) Date of Patent: May 23, 2006

(54) ATTACHABLE SURGICAL ACCESSORY INSTRUMENT

(76) Inventor: Sol Wiess, 7012 Reseda Blvd., Suite A, Reseda, CA (US) 91335

( * ) Notice: Subject to any disclaimer, the term of this patent is extended or adjusted under 35 U.S.C. 154(b) by 373 days.

(21) Appl. No.: 10/122,450

(22) Filed: Apr. 13, 2002

(65) Prior Publication Data

US 2002/0177842 A1    Nov. 28, 2002

Related U.S. Application Data

(60) Provisional application No. 60/286,750, filed on Apr. 26, 2001.

(51) Int. Cl.
*A61B 17/42* (2006.01)
(52) U.S. Cl. .................... 606/119; 600/231; 606/191
(58) Field of Classification Search .............. 600/201, 600/219, 224, 231; 606/119, 205, 210, 211, 606/120, 121, 122, 191
See application file for complete search history.

(56) References Cited

U.S. PATENT DOCUMENTS

| 3,019,790 A | * | 2/1962 | Militana |
|---|---|---|---|
| 3,320,948 A | * | 5/1967 | Martin |
| 3,513,835 A | * | 5/1970 | Ceuster |
| 4,085,756 A | * | 4/1978 | Weaver ................. 128/303.17 |
| 4,185,636 A | * | 1/1980 | Gabbay et al. ......... 128/334 R |
| 4,323,057 A | * | 4/1982 | Jamieson ..................... 128/17 |
| 4,432,352 A | * | 2/1984 | Wineland .................... 128/17 |
| 4,502,485 A | * | 3/1985 | Burgin ....................... 606/191 |
| 4,559,944 A | * | 12/1985 | Jaeger ........................ 128/344 |
| 5,037,430 A | * | 8/1991 | Hasson ....................... 606/119 |
| 5,167,222 A | * | 12/1992 | Schinkel et al. .............. 128/17 |
| 5,217,007 A | * | 6/1993 | Ciaglia .................. 128/207.29 |
| 5,868,668 A | * | 2/1999 | Weiss ......................... 600/224 |
| 5,897,491 A | * | 4/1999 | Kastenbauer et al. ....... 600/239 |
| 6,113,536 A | * | 9/2000 | Aboul-Hosn et al. ....... 600/231 |

* cited by examiner

*Primary Examiner*—Anhtuan T. Nguyen
*Assistant Examiner*—Charles Sam
(74) *Attorney, Agent, or Firm*—Mitchell Silberberg & Knupp LLP

(57) ABSTRACT

A surgical assisting instrument and device having an elongated rectangular u-shaped body with fasteners extending outward therefrom. These fasteners can be of any number and mounted on the top or sides of the body. The body is affixed vertically on the long handle of a tenaculum or other similar elongated handles of surgical clasping instruments. This permits such surgical clasping devices to be anchored or braced onto a fixed surgical device to provide the surgeon with auxiliary clasping and holding assistance.

7 Claims, 6 Drawing Sheets

Figure 5
Figure 6
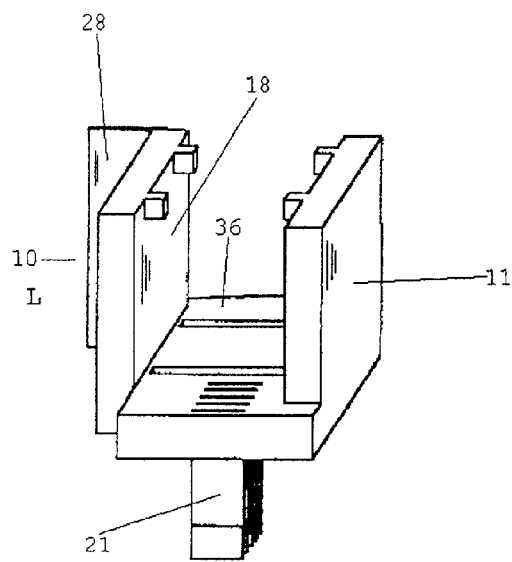
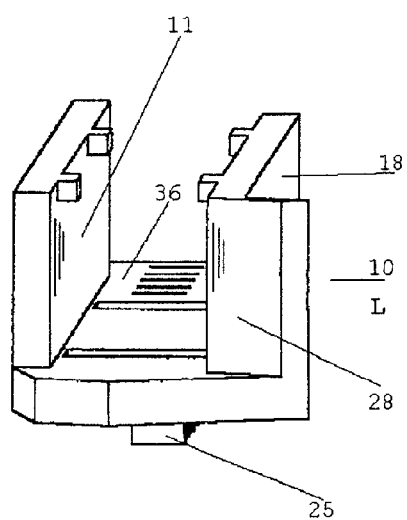

ATTACHABLE SURGICAL ACCESSORY INSTRUMENT

CROSS REFERENCE TO RELATED APPLICATIONS

This application contains subject matter of my provisional application Ser. No. 60/286,750 filed Apr. 26, 2001, entitled Attachable Surgical Accessory Instrument.

BACKGROUND OF THE INVENTION

1. Field of Invention

The invention relates to surgical devices and more specifically to clasping and other similar instruments with elongated handles for use in attachment to rigid and supporting adjunct instrumentation. Such attachment allows for fewer hands and affords, a clamping or holding when required in connection with a surgical procedure.

2. Related Art

During the development of the vaginal speculum of the type which is the subject of my U.S. Pat. No. 5,868,668 and my present pending application No . . . it was realized that tenaculums and other instruments that are inserted into the opening enlarged by the speculum require means to positively affix them to the speculum. There are numerous surgical procedures that require two or more instruments to be used. For example grasping, retracting, sewing, etc. tissues during surgical procedures. Examining vaginal and other cavities may require two or more long handled instruments to be used in conjunction with the desired speculums, which have in their structures a frame that can be used for attachment of the elongated handles of the instruments. This lessens the necessity of additional assistants during procedures. During a surgical procedure, the surgeon often requires sources of lighting, a suctioning catheter with handle irrigation tubes with attachments. Accordingly, it is highly desirable that these multiple instruments be attached to a readily accessible device so that these instruments can be available for use at a moment's notice. In addition the use of multiple instruments that can be readily available and selectively configured for a specific use will allow the surgeon convenience and less cost in doing the surgery. Such a device will also provide the surgeon more freedom and comfort so that instrument will not require additional personnel to assist or even allow instruments that might fall from the area of surgery. This device will also help the surgeon by keeping the instruments available for immediate use while minimizing any obstruction of view and manipulation of the surgical site. Such a device will also have locking capabilities and may be made for permanent use and/or disposable handling for simplicity of use.

BRIEF DESCRIPTION OF THE DRAWING

FIG. 3*a* depicts a right bottom view and FIG. 3*b* shows a similar attachment device but is a generally reverse or mirror image to that of FIG. 3*a*;

FIG. 5 is a front perspective view of the within attachment device.

FIG. 6 is a rear perspective view of the within attachment device; and

Figure 1:
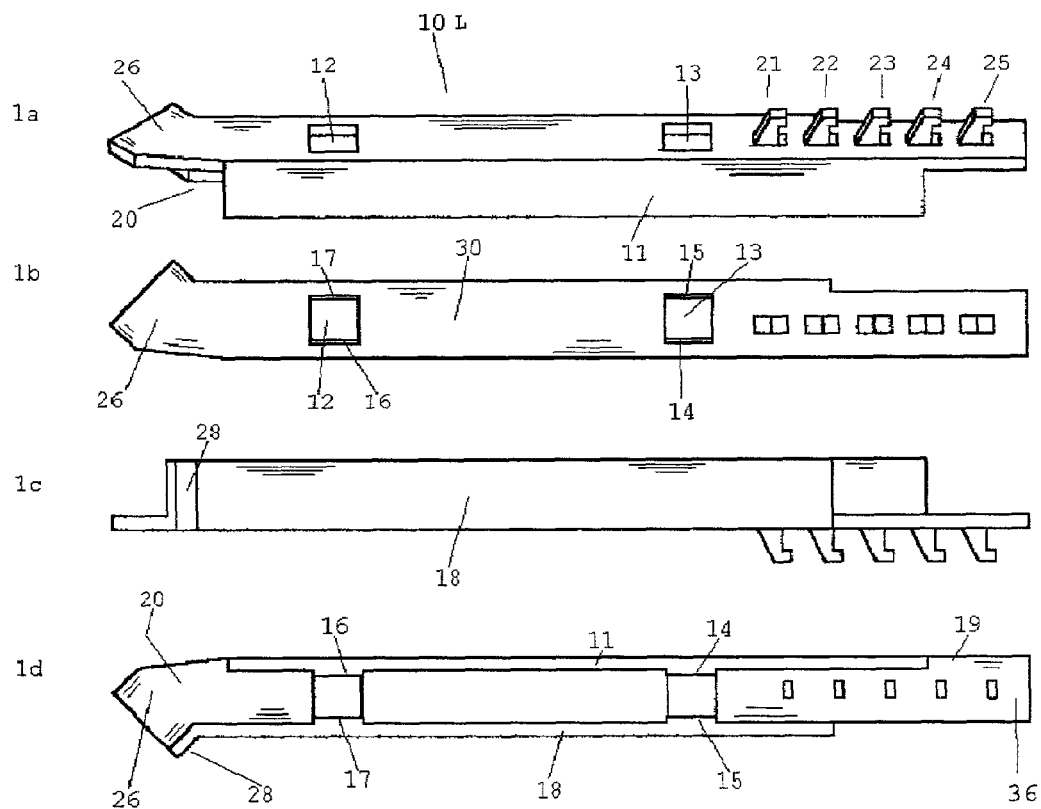
FIG. 1 depicts a series of four views of the invention, a surgical instrument attachment device with FIG. 1*a* being a side perspective view, FIG. 1*b* being a top view, FIG. 1*c* being a side view of the side shown in FIG. 1*a* and FIG. 1*d* is a bottom view.

The applications of the within invention are many. For example, a common surgical procedure requires tension to be maintained on tissues being surgitized, such as, a dilation and curettage (D&C) of the uterus procedure when the cervix portion of the uterus is held under tension. To accomplish this with the present invention, the cervix is grasped and clamped by the prongs of the tenaculum and pulled forward. To maintain the clamping and tension, the within attachment device is secured to the tenaculum and are locked together into the aperture of the yoke portion of the vaginal instrument maintaining the clamped position while executing the D&C procedure.

Neurosurgeons while performing spinal surgery may require tenaculums to hold layers of tissues with grasping, clamping and maintaining tension for retraction and keeping exposure of the operative site available. Thoracic surgeons while doing lung and cardiovascular surgeries will find similar advantages. General surgeons, vascular surgeons, urologists and gynecologists (includes obstetrical procedures) will find benefits when utilizing the within attachment device while performing procedures in the abdominal cavity, such as, for example, appendectomies, nephrectomies, colectomies, cesarean section (delivering babies surgically), aneurysmectomies, etc. Orthopedic surgeons could use the within attachment device with spinal procedures hip surgeries which both require grasping, clamping and tension actions when performing surgery in deep structured areas.

While the present invention is susceptible of various additional modifications and alternative constructions, illustrative embodiments are shown in the drawings and will herein be described in detail. It should be understood however, that it is not to be intended to limit the invention to the particular forms disclosed, but, on the contrary, the intention is to cover all modifications, equivalents, and alternative construction falling within the spirit and scope of the invention as expressed in the appended claims.

DESCRIPTION OF THE PREFERRED EMBODIMENT

Figure 7:
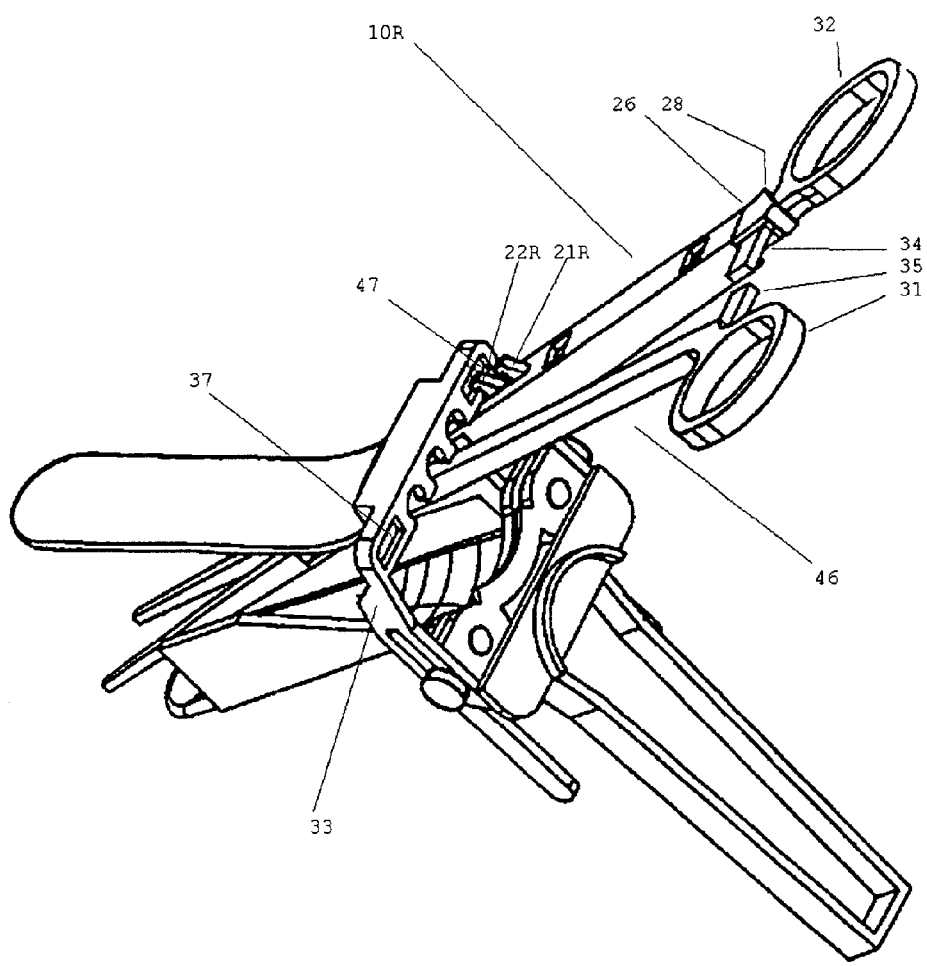
FIG. 7 shows the within attachment device in use and attached to a speculum type of medical instrument.

Referring now to FIG. 1, a surgical attachment device, 10L, carrying out the principles of the instant invention are illustrated in four views. This surgical attachment device 10L, has in FIG. 1*a*, a proportionately positioned series of hook projections, 21, 22, 23, 24 and 25 on the top front side of the body of the attachment device, which serves to attach the device, 10L, to compatible surgical instruments as shown in FIG. 7. In other applications for these hooks to properly function, it has been found that the hooks must have variable heights that will allow attachment to the cooperating member and ensure proper alignment, clearance and solid locking. The apertures 12 and 13 in FIG. 1*b* allows the construction of the stabilizing rails 14, 15, 16 and 17 within the housing of device 10L, so as to permit only non rotational movements as it rests on the handles of other instruments. The flanged portion 26, and the lip edge, 28 of the attachment device, 10L allows it to engage and lock onto the ringed handle portion 31 of tenaculums and other similar devices as shown in FIG. 7. The bottom view of FIG. 1d shows the edge of the housings' inner side wall, 11. The outer housing wall's edge, 18, is shown in FIG. 1c and FIG. 1d.

Figure 2:
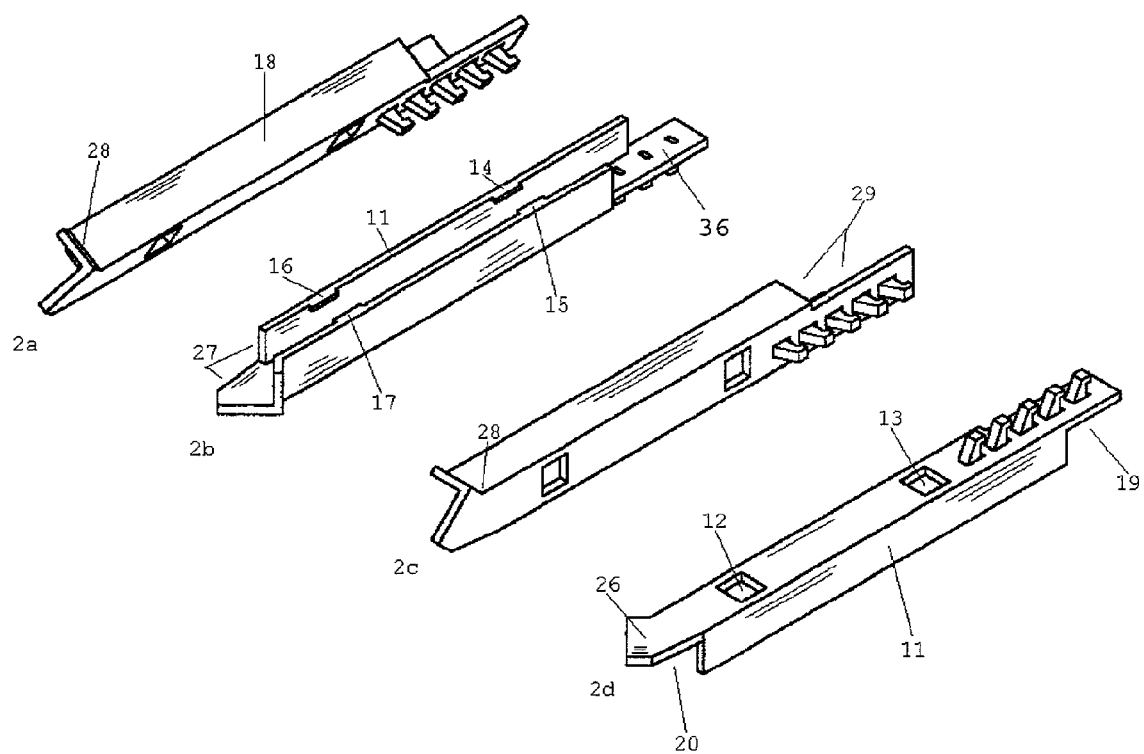
FIG. 2 shows a series of four perspective views taken by rotating the within attachment device above a longitudinally with FIG. 2*a* showing the left side and top, FIG. 2*b* showing the lower surface of the top and both sides, FIG. 2*c* showing the left side and top, and FIG. 2*d* showing the top and right side.

In FIG. 2, a series of four perspective views illustrates the rotation of the left handle side attachment device as shown in FIG. 3b. In FIG. 2a the outer wall 18 also shows the flanging of the rear portion wall 28 that braces against the finger rings of the tenaculum or other instrumentation as seen in FIG. 7. FIG. 2b reveals the cut out 27, the inner rear of device 10L that locks onto the left ring handle of the tenaculum 31 while the right ring handle 32 would serve the right device, 10R. In FIG. 2c the flanged edge 28 of the rear portion for engaging the ringed handle is more clearly depicted. In the outer wall of device 10L, a cut out 29 is provided to allow this side of the device clearance from the outer wall, 33. In FIG. 2d the cut out 19 at the front inner side of device 10L keeps the handles closing freely without obstruction. The cut out 20 in sidewall 11 allows the attachment device 10L to engage the inner ring handle 31 without obstruction to the closing of the ratchet or saw-toothed portions 34 and 35 of the tenaculum to lock the right and left handles.

Figure 3:
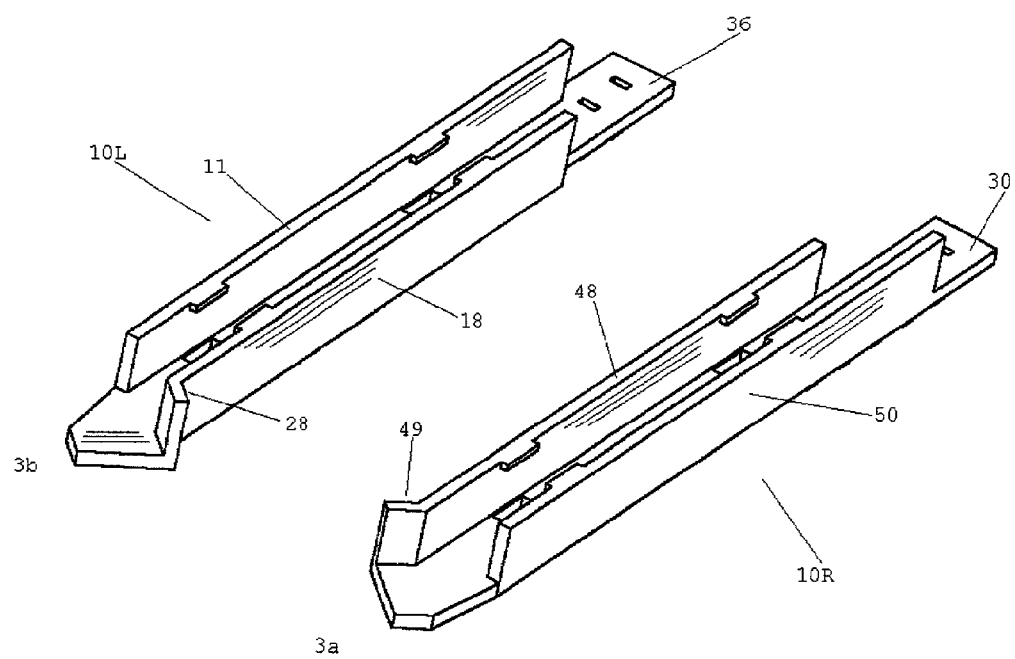
FIG. 3 shows a pair of perspective views with instruments.

FIG. 3 shows the right and left or mirror image 10R of the device, 10L. FIG. 3b shows the inner side 36 of the top portion of device 10L and the inner portion of the top, 30 in the FIG. 3a of right attachment device 10R. The attachment device 10R, a right mirror image of device 10L shows respective inner wall 50, an outer wall 48 and a flanged portion 49.

Figure 4:
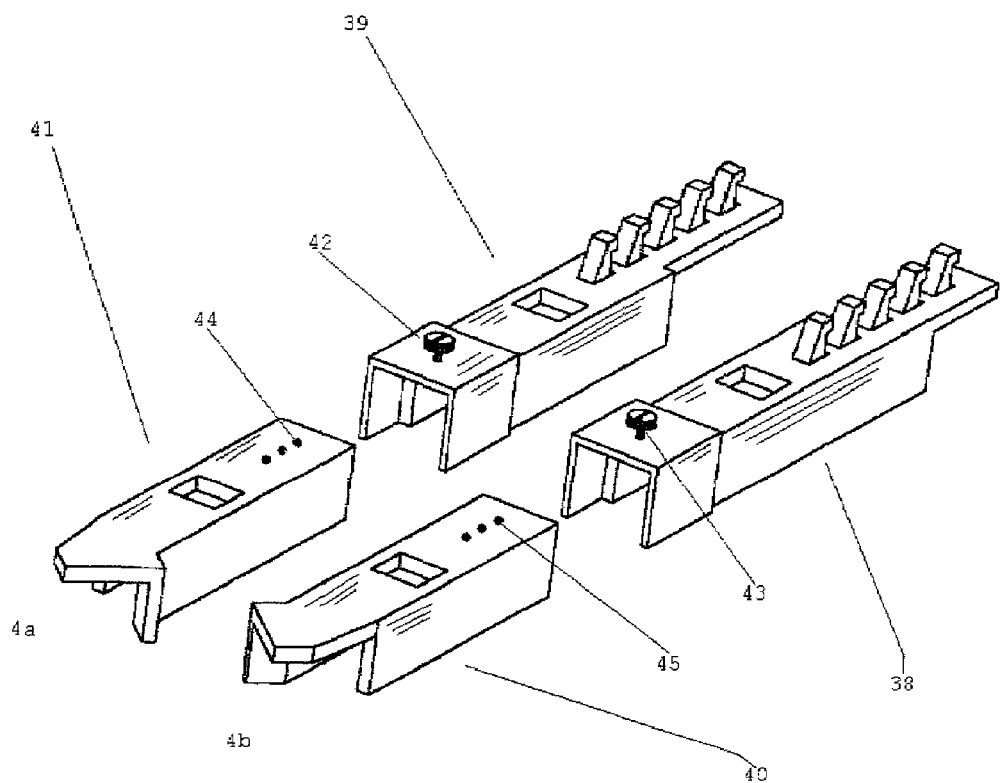
FIG. 4 is a pair of perspective views with FIG. 4*a* showing a top and right side with length adjusting (projecting) provision and FIG. 4*b* showing a similar attachment device but is a generally reverse or mirror image to that of FIG. 4*a*.

FIG. 4a, is a left-sided device, but in two sections 39 and 41 of a device resembling 10L when integrated and locked into position. This occurs when screw 42, is rotated clockwise into any of the plural mating apertures, 44. This allows a variance of length in the bodies depending on the length of the handle portions of tenaculums or other like instruments that are used. When elements 39 and 41 or mirror images 38 and 40 are connected, they will acquire the construction of attachment device, 10L and 10R respectively.

In FIG. 5 the attachment device 10L is shown in a front view with its respective constructions 11, 18, 21, 28, 36 appropriate to this device as previously discussed.

In FIG. 6 the rear view of attachment device 10L and the respective components, 11, 18, 25, 28 and 36 are shown.

In FIG. 7 the within attachment device 10R is shown in an operative position resting on the right handle of a tenaculum 46 and positioned against the finger ring portion 32. The hook projection 22R is advanced into the aperture 47 of the right side of the yoke, (37 on left side of yoke respectively), for locking purposes. The tenaculum 46 is of the type shown in my U.S. Pat. No. 5,868,668 although any surgical instrument provided with apertures that cooperate with the within attachment device could be utilized.

The within attachment devices 10R constructions 38, 40 and 10L constructions 39, 41, (when locked together) may be constructed of rigid material such as plastic, e.g. polycarbonate; polypropylene; metal or a combination thereof.

The hooks 21 thru 25 may be of varying sizes and arrangements so as to accommodate other applications as required in surgical procedures. It is pointed out that while the within embodiment of the present invention is described as utilizing hooks that cooperate with apertures to secure the attachment device to a surgical instrument, it would be well within the spirit and scope of the present invention to utilize equivalent attachment means. The applicability of the within attachment devices to surgical instruments that apply tension or locking affords an excellent service for the surgeon and a cost-effective result for the procedure as described earlier.

What is claimed is:

1. An attachment device for use with surgical clamps that rests on the handle of such clamps while maintaining the position and/or tension of such clamps comprising:
   a) A generally u-shaped elongated body adapted to overlie a portion of the handle of said clamp, and
   b) A plurality of hook means affixed to and extending from said elongated body, and stabilizing means to assist in maintaining the engagement of said elongated body onto said clamp,
   wherein said elongated body is formed in two cooperating engageable sections and locking means whereby the overall length of said elongated body can be selectively chosen and maintained.

2. The attachment device as set forth in claim 1 but as a mirror image of same so as to perform the same function with the other handle of said clamp.

3. The attachment device as set forth in claim 1 whereby said selective maintenance of the length is achieved by means of a locking set screw.

4. An attachment device for use with a surgical clamp, comprising:
   a) An elongated body adapted to overlie a portion of a handle of said surgical clamp and having a generally u-shaped cross-section,
   b) A plurality of hooks extending from said elongated body along the length of said elongated body, and
   c) stabilizing means to assist in maintaining the engagement of said elongated body onto said surgical clamp,
   wherein said elongated body is formed in two cooperating engageable sections whereby the overall length of said elongated body can be selectively chosen.

5. The attachment device as set forth in claim 4 further comprising locking means for maintaining a selected overall length.

6. An attachment device for use with a surgical clamp, comprising:
   a) an elongated body;
   b) means for securing said elongated body to a portion of a handle of said surgical clamp; and
   c) a plurality of fasteners extending from said elongated body along the length of said elongated body,
   wherein said elongated body is formed in two cooperating engageable sections whereby the overall length of said elongated body can be selectively chosen.

7. The attachment device as set forth in claim 6 further comprising locking means for maintaining a selected overall length.

* * * * *